(12) United States Patent
Gros

(10) Patent No.: US 9,909,012 B2
(45) Date of Patent: Mar. 6, 2018

(54) ANTIMICROBIAL INKS AND SEALANTS

(71) Applicant: Robert Timothy Gros, London (GB)

(72) Inventor: Robert Timothy Gros, London (GB)

(*) Notice: Subject to any disclaimer, the term of this patent is extended or adjusted under 35 U.S.C. 154(b) by 0 days.

(21) Appl. No.: 14/899,576

(22) PCT Filed: Jun. 5, 2014

(86) PCT No.: PCT/GB2014/000267
§ 371 (c)(1),
(2) Date: Dec. 18, 2015

(87) PCT Pub. No.: WO2014/202941
PCT Pub. Date: Dec. 24, 2014

(65) Prior Publication Data
US 2016/0160058 A1    Jun. 9, 2016

(30) Foreign Application Priority Data
Jun. 18, 2013  (GB) .................................. 1310852.7

(51) Int. Cl.
| | | |
|---|---|---|
| C09D 5/14 | (2006.01) | |
| C09D 11/03 | (2014.01) | |
| C09D 11/00 | (2014.01) | |
| C09D 11/023 | (2014.01) | |
| A01N 31/08 | (2006.01) | |
| A01N 33/12 | (2006.01) | |
| A01N 35/02 | (2006.01) | |
| A01N 37/36 | (2006.01) | |
| A01N 43/80 | (2006.01) | |
| C09D 11/033 | (2014.01) | |

(52) U.S. Cl.
CPC ............... *C09D 5/14* (2013.01); *A01N 31/08* (2013.01); *A01N 33/12* (2013.01); *A01N 35/02* (2013.01); *A01N 37/36* (2013.01); *A01N 43/80* (2013.01); *C09D 11/00* (2013.01); *C09D 11/023* (2013.01); *C09D 11/03* (2013.01); *C09D 11/033* (2013.01)

(58) Field of Classification Search
None
See application file for complete search history.

(56) References Cited

U.S. PATENT DOCUMENTS

| | | | | |
|---|---|---|---|---|
| 2004/0024037 A1* | 2/2004 | Ryu | ....................... | C09D 11/38 514/394 |
| 2013/0029884 A1* | 1/2013 | Malchesky | ............ | A01N 31/08 507/219 |

FOREIGN PATENT DOCUMENTS

| | | | | |
|---|---|---|---|---|
| EP | 1512408 A1 | 3/2005 | | |
| GB | 2338651 A | 12/1999 | | |
| GB | 2457322 A | 8/2009 | | |
| GB | 2515473 A * | 12/2014 | ............. | A01N 35/02 |
| WO | 02062142 A1 | 8/2002 | | |
| WO | 2008135085 A1 | 11/2008 | | |
| WO | 2012146917 A1 | 11/2012 | | |

\* cited by examiner

*Primary Examiner* — Peter A Salamon
(74) *Attorney, Agent, or Firm* — Finnegan, Henderson, Farabow, Garrett & Dunner, LLP

(57) ABSTRACT

Antimicrobial inks, sealants, coatings or varnishes that are manufactured in three distinct phases: Phase 1, which is an oil phase comprising Ethoxylate Alcohol Laureth 7, Didecyldimethylammonium chloride, Glutaric acid dialdehyde, *Pinus sylvestris*, Alkyldimemylberizylammonium chloride, Parachlorometaxylenol, Ethylenediaminetetraacetic acid, 2-Hydroxypropanoic acid, Hydroxy-9-cis-octadecenoic acid, Cetyl alcohol wax, Octadecenoic acid, Palmityl alcohol, and Epoxy-cis-9-octadecenoic acid; Phase 2, which is a micro-emulsion phase comprising Ethoxylate Alcohol Laureth-7, Cetyl alcohol wax, *Pinus sylvestris*, and Propan-2-ol and Phase 3, which combines the products of Phases 1 and 2 with a base to produce the ink, sealant, coating or varnish.

6 Claims, No Drawings

ANTIMICROBIAL INKS AND SEALANTS

TECHNICAL FIELD

The invention involves a process and constituents used to manufacture antimicrobial additives that can be added to sealants, inks, coatings and varnishes, primarily for use in lithographic and gravure printing, in order to make these mediums antimicrobial.

BACKGROUND ART

Rotogravure (Roto or Gravure for short) is a type of printing process that involves engraving the image on to an image carrier. In gravure printing, the image is engraved onto a cylinder because it uses a rotary printing press. Once a staple of newspaper photo features, the rotogravure process is still used for the commercial printing of magazines, postcards, and the printing of cardboard product packaging.

The general principles in offset lithography are identical to traditional metal plate lithography. The difference between them is in the manner by which they are printed. Various offset printing presses may have different roller systems but all share three major components: a plate cylinder that holds the printing plate, a blanket cylinder wrapped in rubber that carries the image to be transferred, and the impression cylinder which applies the pressure to print the image. A gear train connects all three cylinders together so they are in perfect synchrony with one another. Printing begins when a processed litho-plate containing an image is mounted on a cylinder, mechanically dampened with a wetting agent, and then rolled with ink. The oily ink is repelled from the damp areas and is attracted to the dry image areas. A blanket cylinder is then rolled over it, picking up the inky image onto its soft rubber surface. Paper then passes between this blanket cylinder and the hard impression cylinder, which presses all three surfaces together, transferring the image to the paper. Previously the printing plate and paper needed to make perfect contact but here the soft blanket can pick up and deposit ink much better than a hard surface, creating impressions on almost any material with greater fidelity. Even though the first offset press was built in 1904, the method only became popular after 1951 when an easy to use, storable, photosensitive aluminum litho-plate was developed. Offset lithography quickly became the standard in photochrome postcard production. Nearly all postcards produced today are made through process printing on offset lithography presses, though they have largely been adapted to digital technology. Lithography is a method of printing using a metal plate with a completely smooth surface. In modern lithography the image is made of a polymer coating applied to a flexible aluminium plate.

Mechanically produced packaging has been, used in printing technology for the last hundred years. As new technology has emerged, modern packaging, printed material and pulp based mediums are now sealed with a clear varnish or sealant. The concept of the sealant is to seal any ink to the surface of printed medium.

Most inks have a low threshold for being rubbed off or smudged. They are also susceptible to moisture and have limited luminescence. The sealing coat prevents the ink from being rubbed off, reduces smudging, and helps to brighten up the inks. Sealants are all applied post production. Any other process that includes additives in the pulping process is as a pre-treatment.

There are three distinct types of sealant: Hydrocarbon oil phase, Aqueous phase, and Poly acrylic. All them are focused on pre treating the paper or packaging board for the purpose of protecting the surface of the paper or board and making them free from contamination prior to printing. A small number claim residual activity by the use of preservatives placed in the pulp prior to formation into board or paper stock. These are specialist products commanding a premium price and have very specific applications.

The printing process is a method of placing ink on to a surface. The use of a sealant or varnish placed on to a printed surface is designed to fulfill a number of purposes. It is designed to increasing the speed of printing to allow for the sheets to be printed on both sides to improve the finish of the printed medium and to protect the ink from rub off or smudging.

Presently there are no print finishes designed for creating an antimicrobial print finish used in packaging construction or in the print finishing industry.

DISCLOSURE OF INVENTION

The present invention provides a novel method of incorporating antimicrobial compounds in to existing coatings sealants, inks, coatings and varnishes used in commercial procedures for coating printed products. The unique method of incorporation can reduce colonisation of micro-organisms. In some applications this may help prevent the spread of microbial contamination and infections.

Special manufacturing processes are used to rapidly cure the sealant, inks coatings or varnishes thereby making them suitable for high speed printing processes. By incorporating the antimicrobial substrate a sustainable coating for all pulp based manufacture can be provided.

The coating is manufactured by adding unique resins, acrylics or poly acrylates to a substrate to form a hydrocarbon based oxidation cured coating or an aqueous based UV (ultraviolet) or IR (infrared) cured ink or sealant.

The unique antimicrobial system has been created to work with any and all of the existing coating sealants and ink based products. A number of constituents (biocides and surfactants) were assessed for their possible use in the ink or sealant that will be used to coat the pulp, paper and card product or packaging with antimicrobial capabilities.

The sealant (coating) has unique applications within the design criteria of print sealing. They relate to reducing the potential for any printed or prepared surface to hold a microbial loading, provide technical advancement in the concept of printed mediums and in specific applications provide unique practical advancement in infection control utilising packaging rather than mechanical intervention therefore reducing expensive and impracticable processes to achieve hygienic environments.

The coating process will render a surface free of microbiological contamination including bacteria, viruses and fungi. The coating systems are able to provide excellent protection against a wide range of contaminants in addition to being an effective barrier against blood-borne and aspirated pathogens.

As with conventional print coatings, inks and sealants, our system has been assessed to match or improve existing physical protection of the printed surface. The unique additional benefits are also supplemented by providing highly effective barrier protection and resistance.

The key benefit is, however, that it provides permanent protection of the product that had previously been unattainable with the conventional commercial processes and products. The principle behind the coating is to provide a microbial bather between the external environment and the packaging, thereby further protecting the contents and the packages surface from contamination.

Antimicrobial agents are incorporated into the coating, ink, sealant or varnish and transferred on to the pulp surface structure and/or print medium via existing commercially practiced methods. This may be but is not exclusive to block printing, colour printing, etching, flexography, letterpress printing, lineography, photochromic, lithography using MeV ions—Proton beam writing, four-color lithographic press, Rotogravure, Seri lithograph, Stencil lithography, but may also be represented by other methods including Typography.

Some systems have explored addition processes, such as pre-coating the paper or pulp mediums with expensive and uneconomic additional stages and or components. However, these additional stages restrict flexibility and are generally understood to be cost prohibitive and mechanically impracticable.

The manufacturing process is novel because the antimicrobials are uniquely fixed on to the surface via an innovative coating system of the pulp for optimum effect. The process of creating micro emulsions and micro dispersions operates across a diverse polarised phase, thereby creating a high molecular weight substrate.

Introducing anionic components to cationic components would traditionally render them inactive. By creating two completely separate phases we have developed a process that enables the two ionic charges operating concurrently by a process of converting the anions to a cation within a traditional coating system. The unique chemistry integrates with conventional sealant technology.

The surfactants within the formulation create colloids within the technology, which, when combined with the active ingredients, balance out polarity and provide cationic proliferation simultaneously occupying the same space. Thus we have a cationic phase operating within the hydrophilic level and an anionic phase operating within the hydrophobic phase. The significance of this is that surface borne pathogens that sample their environment through diffusion are rendered inactive via toxification. Organisms that operate in the hydrophobic phase are deactivated through ionic exchange and protein disruption.

Chemical Principles

Traditional sealants rely on attraction from one surface to another. The present invention creates a coating that manipulates the ionic bonding. Plastic and varnish coated substrates are difficult to bond because they are "hydrophobic" (not naturally wettable), possess poor surface wettability (low surface energies), non-polar-inert structures and possess poor surface-chemical functionality.

The contact angle is the angle formed by the solid surface and the tangent line to the upper surface at the end point. Physical properties of interaction between solids and liquids provide valuable information in determining optimal adhesion bonding and surface wettability conditions. The angle formed by the solid surface and the tangent line to the upper surface at the end point is called the contact angle. It is the angle between the tangent line at the contact point and the horizontal line of the solid surface.

Our invention optimizes the traditional method of printing using attraction and surface tension with the unique ability to precisely standardize the distribution coefficient of biocides within the manufactured sealant. Random distribution would be unacceptable within our process.

The optimum coverage rate is between 1.2 grams per square meter and 2.2 grams per square meter dependent on the quality of the paper or board being coated and the material finish. The bubble/droplet shape is due to the molecular forces by which all liquids, through contraction of the surface, tend to form the contained volume into a shape having the least surface area. The intermolecular forces that contract the surface are termed "surface tension." Surface tension, a measurement of surface energy, is expressed in "dynes/cm" (or mN/m SI units).

Summary of Constituent Choices

The selected chemicals have been identified for their antimicrobial activity and their dynamic interaction between the active ingredients and the sealants, inks, coatings and varnishes. Our method of uniformed distribution of antibacterial agents using a cationic or non-ionic solution, creates a micro-emulsion or enables the antimicrobial agents to be added to the sealant solution and to physically and chemically bond the active ingredients uniformly to the surface of the sealant.

The interaction between the coating and active substrate is critical. It is not feasible to just suspend all of the materials in the sealant as this results in deactivation of some of the antimicrobial components due to polar incompatibility. The antimicrobial ingredients might also interfere with the coating process. The selection of the antimicrobial agents is critical during the fixing process of the sealant because the incorrect selection or distribution of the active substances will result in a compromise in the integrity and the efficacy of the product. The careful design of the composition of the antimicrobial blend ensures the continued smooth operation of the manufacturing process.

The unique dispersion method in the solution prevents the active ingredients from coming into contact with the ingredients in the coating and aids the uniform incorporation of the antimicrobial agents on to the substructure and surface of the packaging.

We have developed a process that incorporates a synergistic mixture of biocidal agents into the coating by adding a specially formulated mixture of biocides. The composition of both hydrophilic and hydrophobic ingredients creates a micro-emulsion suspension this needs to be very carefully controlled to ensure that they perform as required. The approaches required for the two suspensions simultaneously held in a single suspension are quite different and so must be chosen very carefully. It is important that whatever is added to either suspension does not interfere with the coating manufacturing and making process.

Individual biocidal agents destroy particular infectious microorganisms. To ensure the treated surface destroys the broad, range of infections they are likely to experience the coating needs to contain a careful selection of biocidal agents that can be held in a micro emulsion phase. Other biocidal agents can be formulated into either suspension. Each biocide kills the bacteria in different ways and so mixtures will have synergistic effects. Many biocides are insoluble in water and or oil therefore need to be dispersed into the two suspensions without adversely affecting their stability and the formation of the coating. These agents are incorporated in the ratio and the location that is most effective at destroying microorganisms.

In addition to conventional biocides we have also selected components that will break down the protein structure and lipid layer of the outer shell of micro-organisms, which is a unique feature for a permanent structure (print surface). Because of the compatibility issues the uses of some of the agents are restricted and may only be available for use in certain parts of the coating manufacturing process. Some antibacterial substances are soluble or are available as stable dispersions and can be readily added to the aqueous phase.

Others are difficult to disperse into water and therefore need dispersing using particular combinations of surfactant stabilising agents and technology.

Constituents

Below is a list of constituents that have been selected following a number of detailed studies to find the most suitable for the process. Also detailed are the common names, the optimal volumes, the preferred range of volumes, and the mode of action. Other constituents from the same group of chemicals could substitute for the chosen constituents to a lesser extent. However, their substitution would result in reduced efficacy because of their lesser activity and suitability:

Chemical name: Didecyldimethylammonium chloride
Common Name: DDAC—1010e
Lesser substitutes: Ammonium chloride quaternary amines
Optimal volume in Phase 1: 3.3%
Preferred range in Phase 1: 2% to 5%
Mode of action: The mechanism of bactericidal and microbicidal action is thought to be due to disruption of intermolecular interactions. This can cause dissociation of membrane lipid bilayers, which compromises cellular permeability controls and induces leakage of contents. Other bimolecular complexes within the bacterial cell can also undergo dissociation.

Chemical name: Alkyldimethylbenzylammonium chloride
Common name: Benzylkonium chloride (BTC 50e)
Lesser substitutes: Ammonium chloride quaternary amines
Optimal volume in Phase 1: 5.4%
Preferred range in Phase 1: 3% to 6%
Mode of action: Activity is associated with the C12 dodecyl & C14 myristyl alkyl derivatives. The mechanism of bactericidal/microbicidal action is thought to be due to disruption of intermolecular interactions. This can cause dissociation of membrane lipid bilayers, which compromises permeability controls and induces leakage of cellular contents. Other biomolecular complexes within the bacterial cell can also undergo dissociation.

Chemical name: Glutaric acid dialdehyde
Common name: Pentane-1,5-dial
Lesser substitutes: Aldheydes
Optimal volume in Phase 1: 5.5%
Preferred range in Phase 1: 3% to 6%
Mode of action: The principle metabolic mode of action is to disrupt proteins and lipid assemblies in both internal and external cell structures. It was proposed that the metabolism probably involved initial oxidation to corresponding carboxylic acids by aldehyde dehydrogenase, and then further oxidation to CO2.

Chemical name: Parachlorometaxylenol
Common name: PCMX
Lesser substitutes: Chlorophenols
Optimal volume in Phase 1: 4.4%
Preferred range in Phase 1: 2% to 6%
Mode of action: PCMX has been demonstrated to be effective against bacteria, virus, and fungal species. In other formulations using PCMX, its biocide activity has been limited due to the inability of such formulations to deliver PCMX through the microorganism's cell membrane because a water barrier exists between the membranes, which are both oily. Our chemical emulsion technology efficiently enables the delivery of PCMX across this barrier to the cell membranes.

Chemical Name: Ethylenediaminetetraacetic acid
Common name: EDTA
Lesser substitutes: Chelates
Optimal volume in Phase 1: 6.2%
Preferred range in Phase 1: 2% to 7%
Mode of action: Coordination chemistry, EDTA4- is a member of the polyamino carboxylic acid family of ligands. EDTA4- usually binds to a metal cation through its two amines and four carboxylates. Many of the resulting coordination compounds adopt octahedral geometry. Although of little consequence for its applications, these octahedral complexes are chiral. The anion has been resolved into enantiomers. Many complexes of EDTA4- adopt more complex structures due to the formation of an additional bond to water, such as seven-coordinate complexes, or the displacement of a carboxylate arm by water.

Chemical name: 2-Hydroxypropanoic acid
Common name: Lactic Acid
Lesser substitutes: Organic acids
Optimal volume in Phase 1: 3.7%
Preferred range in Phase 1: 1% to 4%
Mode of action: The key basic principle on the mode of action of organic acids on bacteria is that non-dissociated (non-ionized) organic acids can penetrate the bacteria cell wall and disrupt the normal physiology of certain types of bacteria that we call pH-sensitive. This means that they cannot tolerate a wide internal and external pH gradient. Among those bacteria are *Escherichia coli*, *Salmonella* Species *pluralis*, *Clostridium perfringens*, *Listeria monocytogenes*, and *Campylobacter* species.

Chemical name: Ethoxylate Alcohol, Laureth-7
Common name: Alcohol ethoxylate
Lesser substitutes: Non-ionic surfactants
Optimal volume in Phase 1: 14.2%
Preferred range in Phase 1: 5% to 22%
Optimal volume in Phase 2: 42%
Preferred range in Phase 2: 22% to 50%
Mode of action: Surfactants are compounds that lower the surface tension of a liquid, the interfacial tension between two liquids, or that between a liquid and a solid. Surfactants may act as detergents, wetting agents, emulsifiers, foaming agents, and dispersants.

Chemical name: Cetyl alcohol wax
Common name: Fatty alcohol (Non-ionic wax)
Lesser substitutes: Fatty alcohols
Optimal volume in Phase 1: 14.2%
Preferred range in Phase 1: 6% to 22%
Optimal volume in Phase 2: 48%
Preferred range in Phase 2: 22% to 50%
Mode of action: Cetyl alcohol is used in the formulation as an opacifier and emulsifier to maintain the colloid system. It takes advantage of the thickening properties that occur similar to the manufacture of skin creams and lotions.

Chemical Name: Hydroxy-9-cis-octadecenoic acid
Common name: Ricinoleic Acid
Lesser substitutes: Fatty alcohols
Optimal volume in Phase 1: 10.9%
Preferred range in Phase 1: 4% to 12%
Mode of action: Fatty acid. It is an unsaturated omega-9 fatty acid used to create the micro emulsion.

Chemical name: Octadecenoic acid
Common name: Oleic acid
Lesser substitutes: Fatty alcohols
Optimal volume in Phase 1: 10.9%
Preferred range in Phase 1: 6% to 12%
Mode of action: A monounsaturated fatty acid used to create the micro emulsion.

Chemical name: Epoxy-cis-9-octadecenoic acid
Common name: Linoleic Acid
Lesser substitutes: Fatty alcohols
Optimal volume in Phase 1: 8.9%
Preferred range in Phase 1: 4% to 11%
Mode of action: A monounsaturated long chain carboxylic acid contains an epoxide cosurfactant used to stabilise the micro emulsion.

Chemical Name: Palmityl alcohol
Common name: Coconut oil soap
Lesser substitutes: Fatty alcohols
Optimal volume in Phase 1: 8.9%
Preferred range in Phase 1: 3% to 10%
Mode of action: Cross link polymer of saponified coconut oil if used to emulsify the water and oil phase of the formulation. This maintains the micro emulsion and colloids that prevent the sealant from separating.

Chemical name: *Pinus sylvestris*
Common name: Pine oil
Lesser substitutes: Terpenes
Optimal volume in Phase 1: 2.5%
Preferred range in Phase 1: 1% to 5%
Optimal volume in Phase 2: 6%
Preferred range in Phase 2: 5% to 7%
Mode of action: The pine oil is used as a solvent within the first key mixing stage it is used as a solubiliser.

Chemical name: Propan-2-ol
Common name: (isopropyl alcohol) and also IPA
Lesser substitutes: Alcohols
Optimal volume in Phase 2: 4%
Preferred range in Phase 2: 2% to 6%
Mode of action: A secondary alcohol in which the alcohol carbon is attached to two other carbons. It is miscible in water, solubilising non-organics natural resins present in the system to maximise distribution of the actives.

Chemical name: Methylchloroisothiazolinone
Common name: Nipacide CFX
Lesser substitutes: Isothiazolinones
Optimal volume in Phase 1: 1.1%
Preferred range in Phase 1: 0.25% to 2%
Mode of action: Used as a preservative with antibacterial and antifungal effects within the group of isothiazolinones. It is effective against gram-positive and gram-negative bacteria, yeast, and fungi.

Testing of Constituents

Testing of all of the constituents used in the present invention demonstrated a synergistic efficacy for both of the two type organisms and the uses that were assessed. Evidence of efficacy was provided in two certificates of analysis by the analysts.

First Certificate of Analysis
Consultant analysts: Abbott Analytical
Received from: Chemical Intelligence Ltd.
Samples: Three samples of coated paper
Certificate number: 13C.077SaKn.CIN
Sample reference: 13C/075-077
Analysis required: ISO 20743—Determination of antibacterial activity
Test bacteria: *Staphylococcus aureus* (NCTC 10788)
Concentration of inoculum: $1.01 \times 10^6$
Sterilisation method: Autoclave
Measuring method: Plate count
Incubation time: 20 hours
Paper Sample 1
At the outset: $8.87 \times 10^5$ ($71 \times 10^{-4}$, $85 \times 10^{-4}$, $110 \times 10^{-4}$), 1 g $T_0$ 5.94
After 20 hours: $5.53 \times 10^2$ ($45 \times 10^{-1}$, $53 \times 10^{-1}$, $68 \times 10^{-4}$), 1 g $T_{20}$ 2.74
Difference of extremes (1 g): $T_0$ 0.04–$T_{20}$ 0.18
Antimicrobial activity (F-G): 3.23
Growth value (G): −3.20
Paper Sample 2
At the outset: $8.87 \times 10^5$ ($81 \times 10^{-4}$, $85 \times 10^4$, $100 \times 10^4$), 1 g $T_0$ 5.94
After 20 hours: $<1.00 \times 10^1$ ($0 \times 10^{-4}$, $0 \times 0 \times 10^{-1}$), 1 g $T_{20} < 1.00$
Difference of extremes (1 g): $T_0$ 0.08–$T_{20}$ 0.00
Antimicrobial activity (F-G): >4.97
Growth value (G): <−4.94
Paper Sample 3
At the outset: $7.60 \times 10^5$ ($75 \times 10^{-4}$, $70 \times 10^{-4}$, $83 \times 10^{-4}$), 1 g $T_0$ 5.88
After 20 hours: $1.23 \times 10^2$ ($14 \times 10^{-1}$, $13 \times 10^{-4}$, $10 \times 10^{-1}$), 1 g $T_{20}$ 2.09
Difference of extremes (1 g): $T_0$ 0.06–$T_{20}$ 0.15
Antimicrobial activity (F-G): 3.82
Growth value (G): −3.79
Control
At the outset: $7.43 \times 10^5$ ($81 \times 10^{-4}$, $70 \times 10^{-4}$, $72 \times 10^{-4}$), 1 g $T_0$ 5.87
After 20 hours: $7.93 \times 10^5$ ($88 \times 10^{-4}$, $75 \times 10^{-4}$, $75 \times 10^{-4}$), 1 g $T_{20}$ 5.90
Difference of extremes (1 g): $T_0$ 0.05–$T_{20}$ 0.07
Growth value (F): 0.03
Test bacteria: *Klebsiella pneumoniae* (NCIMB 10341)
Concentration of inoculum: $8.30 \times 10^5$
Sterilisation method: Autoclave
Measuring method: Plate count
Incubation time: 20 hours
Paper Sample 1
At the outset: $8.87 \times 10^5$ ($65 \times 10^{-4}$, $71 \times 10^{-4}$, $71 \times 10^{-4}$), 1 g $T_0$ 5.84
After 20 hours: $3.07 \times 10^2$ ($28 \times 10^{-1}$, $29 \times 10^{-1}$, $35 \times 10^{-1}$), 1 g $T_{20}$ 2.49
Difference of extremes (1 g): $T_0$ 0.04–$T_{20}$ 0.10
Antimicrobial activity (F-G): 3.41
Growth value (G): −3.35
Paper Sample 2
At the outset: $7.70 \times 10^5$ ($75 \times 10^{-4}$, $71 \times 10^{-4}$, $85 \times 10^{-4}$), 1 g $T_0$ 5.89
After 20 hours: $2.53 \times 10^2$ ($23 \times 10^{-1}$, $25 \times 10^{-1}$, $28 \times 10^{-1}$), 1 g $T_{20}$ 2.40
Difference of extremes (1 g): $T_0$ 0.08–$T_{20}$ 0.09
Antimicrobial activity (F-G): 3.55
Growth value (G): −3.49
Paper Sample 3
At the outset: $7.60 \times 10^5$ ($71 \times 10^{-4}$, $75 \times 10^{-4}$, $82 \times 10^4$), 1 g $T_0$ 5.88
After 20 hours: $6.50 \times 10^2$ ($63 \times 10^{-1}$, $64 \times 10^{-1}$, $68 \times 1$ g $T_{20}$ 2.81
Difference of extremes (1 g): $T_0$ 0.06–$T_{20}$ 0.03
Antimicrobial activity (F-G): 3.13
Growth value (G): −3.07
Control
At the outset: $8.03 \times 10^5$ ($81 \times 10^{-4}$, $75 \times 10^{-4}$, $85 \times 10^{-4}$), 1 g $T_0$ 5.90
After 20 hours: $9.10 \times 10^5$ ($88 \times 10^{-4}$, $90 \times 10^{-4}$, $95 \times 10^{-4}$), 1 g $T_{20}$ 5.96
Difference of extremes (1 g): $T_0$ 0.05–$T_{20}$ 0.03
Growth value (F): 0.06
Second Certificate of Analysis
Consultant analysts: Abbott Analytical
Received from: Chemical Intelligence Ltd Samples: Three samples of paper coated with Antibacterial ink
Certificate number: 13D.126SaKn.CIN
Sample reference: 13D/118, 119, 126
Analysis required: ISO 20743—Determination of antibacterial activity
Test bacteria: *Staphylococcus aureus* (NCTC 10788)
Concentration of inoculum: $2.06 \times 10^6$
Sterilisation method: Autoclave
Measuring method: Plate count
Incubation time: 20 hours
Antibacterial ink (Standard NS4B)
At the outset: $1.49 \times 10^5$ ($141 \times 10^{-3}$, $172 \times 10^{-3}$, $135 \times 10^{-3}$), 1 g $T_0$ 5.17
After 20 hours: $1.26 \times 10^1$ ($116 \times 10^0$, $114 \times 10^0$, $148 \times 10^0$), 1 g $T_{20}$ 2.10
Difference of extremes (1 g): $T_0$ 0.11–$T_{20}$ 0.11
Antimicrobial activity (F-G): 3.04
Growth value (G): −3.07
Antibacterial ink (Mod NS4B)
At the outset: $1.43 \times 10^5$ ($110 \times 10^{-3}$, $138 \times 10^{-3}$, $180 \times 10^{-3}$), 1 g $T_0$ 5.15
After 20 hours: $<1.00 \times 10^0$ ($<1 \times 10^0$, $<1 \times 10^0$, $<1 \times 10^0$), 1 g $T_{20}<0.00$
Difference of extremes (1 g): $T_0$ 0.21–$T_{20}$ 0.00
Antimicrobial activity (F-G): >5.12
Growth value (G): <−5.15
Antibacterial ink (Mod NS4B Intense black)
At the outset: $1.43 \times 10^5$ ($125 \times 10^{-3}$, $148 \times 10^{-3}$, $156 \times 10^{-3}$), 1 g $T_0$ 5.16
After 20 hours: $3.67 \times 10^0$ ($4 \times 10^0$, $1 \times 10^0$, $6 \times 10^0$), 1 g $T_{20}$ 0.56
Difference of extremes (1 g): $T_0$ 0.10–$T_{20}$ 0.78
Antimicrobial activity (F-G): 4.57
Growth value (G): −4.60
Control
At the outset: $1.45 \times 10^5$ ($111 \times 10^{-3}$, $139 \times 10^{-3}$, $184 \times 10^{-3}$), 1 g $T_0$ 5.16
After 20 hours: $1.35 \times 10^5$ ($118 \times 10^{-3}$, $148 \times 10^{-3}$, $139 \times 10^{-3}$), 1 g $T_{20}$ 5.13
Difference of extremes (1 g): $T_0$ 0.22–$T_{20}$ 0.10
Growth value (F): −0.03
Test bacteria: *Klebsiella pneumoniae* (NCTC 10341)
Concentration of inoculum: $1.74 \times 10^5$
Sterilisation method: Autoclave
Measuring method: Plate count
Incubation time: 20 hours
Antibacterial ink (Standard NS4B)
At the outset: $1.31 \times 10^5$ ($117 \times 10^{-3}$, $147 \times 10^{-3}$, $130 \times 10^{-3}$), 1 g $T_0$ 5.12
After 20 hours: $1.27 \times 10^1$ ($17 \times 10^0$, $8 \times 10^0$, $13 \times 10^0$, 1 g $T_{20}$ 1.10
Difference of extremes (1 g): $T_0$ 0.10–$T_{20}$ 0.33
Antimicrobial activity (F-G): −3.99
Growth value (G): −4.02
Antibacterial ink (Mod NS4B)
At the outset: $1.19 \times 10^5$ ($107 \times 10^{-3}$, $134 \times 10^{-3}$, $115 \times 10^{-3}$), 1 g $T_0$ 5.07
After 20 hours: $<1.00 \times 10^0$ ($<1 \times 10^0$, $<1 \times 10^0$, $<1 \times 10^0$), 1 g $T_{20}<0.00$
Difference of extremes (1 g): $T_0$ 0.10–$T_{20}$ 0.00
Antimicrobial activity (F-G): >5.04
Growth value (G): <−5.07
Antibacterial ink (Mod NS4B Intense black)
At the outset: $1.19 \times 10^5$ ($86 \times 10^{-3}$, $144 \times 10^{-3}$, $126 \times 10^{-3}$), 1 g $T_0$ 5.07
After 20 hours: $<1.00 \times 10^0$ ($<1 \times 10^0$, $<1 \times 10^0$, $<1 \times 10^0$), 1 g $T_{20}<0.00$
Difference of extremes (1 g): $T_0$ 0.22–$T_{20}$ 0.00
Antimicrobial activity (F-G): <−5.07
Growth value (G): >5.04
Control
At the outset: $1.14 \times 10^5$ ($85 \times 10^{-3}$, $125 \times 10^{-3}$, $133 \times 10^{-3}$), 1 g $T_0$ 5.06
After 20 hours: $1.08 \times 10^5$ ($90 \times 10^0$, $106 \times 10^0$, $127 \times 10^0$), 1 g $T_{20}$ 5.03
Difference of extremes (1 g): $T_0$ 0.19–$T_{20}$ 0.15
Growth value (F): −0.03

The test criteria for both organisms and both treatments are acceptable. Ink sample Standard NS4B showed a greater than 1 g 3 reduction against both *Staphylococcus aureus* and *Klebsiella pneumoniae*, after 20 hours. Ink sample Mod NS4B showed a greater than 1 g 5 reduction against both *Staphylococcus aureus* and *Klebsiella pneumoniae*. Ink sample Mod NS4B Intense Black showed a greater than 1 g 4 reduction against *Staphylococcus aureus* and a greater than 1 g 5 reduction against *Klebsiella pneumoniae*.

Manufacturing Process

Detailed in the method of manufacture are the three stages of the production process. To calculate the manufacturing requirements we have three separate processes. Phase 1 and phase 2 are the manufacturing stages for the suspension of the active components. Phase 3 is the transfer of the premix fluids in to the final resin or base. The arithmetic values in phase one and phase two are calculated based on the additions for each phase and not as an arithmetic calculation of the end product. The end product calculation is identified in the summary of components expressed in phase three as end points for the materials selected. The first two phases would be carried out simultaneously but for the purpose of describing the invention we have expressed them as separate processes. Each process is vital for the formation of a micro-emulsion. It is the process of dispersion that provides the ability to create a coating that remains uniform, stable and fit for purpose.

The primary invention is the creation of a stable additive to be blended in to a final resin or base. This process has been considered as the most commercially acceptable method. The resin may be Oil resin based, Aqueous resin, Aqueous Acrylic, Silicon resin based and emulsion which is a combination of the Oil and Aqueous resin.

Phase 1: The Micro Emulsion Phase

The micro emulsion phase generates a micelle structure. It is the technique of creating the phase between soluble and insoluble components. The hydrocarbon structure of the resin is hydrophobic and will not bind to the active ingredients without the chemical intervention of our chemistry.

Phase 1 introduces the micro-dispersion phase of the ingredients which is only slightly soluble in water. Integrating a polarised high molecular Chloroxylenol enables us to cross and fix it to the resin base. The polymers used in the process have no biocidal function but provides the emulsion process and when fixed does provide the basis for the invention of an antibacterial coating to work.

Method of Manufacture: Micelle micro dispersion
Addition rate of phase one in to the final resin phase: 4%
Batch Size: 1000 Kg
Ensure all equipment is clean.
All additions are made on a net w/w or w/v of the active value.

1. Charge 4.4% Parachlorometaxylenol in to the primary high speed shearer vessel at ~75° C.

2. Charge 2.5% *Pinus sylvestris*. Blend the product at a rate of 16 grams per second, and no more, and then run until distributed.

3. Charge 10.9% Octadecenoic acid and start the heating process. The melting point is between 40° C. and 50° C. Set the high shear stirring speed of the vessel to 3200 r.p.m. with a run time of 9 minutes.

4. Charge 8.9% Palmityl alcohol. Maintain heating but do not heat to greater than 60° C. Set the high shear stirring speed of the vessel to 3200 r.p.m. with a run time of 9 minutes.

5. Charge 14.2% Ethoxylate Alcohol, Laureth-7 and mix for 4 minutes.

6. Charge 10.9% hydroxy-9-cis-octadecenoic acid. Maintain heating but do not heat to greater than 60° C. Set the high shear stirring speed of the vessel to 3200 r.p.m. with a run time of 9 minutes.

7. Charge 14.2% Cetyl alcohol wax. Maintain heating but do not heat to greater than 60° C. Set the high shear stirring speed of the vessel to 3200 r.p.m. with a run time of 9 minutes.

8. Charge 8.9% Epoxy-cis-Octadecenoic acid. Maintain heating but do not heat to greater than 60° C. Set the high shear stirring speed of the vessel to 3200 r.p.m. with a run time of 9 minutes.

9. Charge 3.7% 2-Hydroxypropanoic acid to de-ionise fatty acid esters. Prepare the colloid micro emulsion phase. Transfer to the cooling vessel. Maintain permanent stirring and start cooling.

10. Charge 6.2% Ethylenediaminetetraacetic acid to the cooling vessel and maintain permanent stirring.

11. Charge 3.3% Didecyldimethylammonium chloride to the cooling vessel and maintain permanent stirring.

12. Charge 5.4% Alkyldimethylbenzylammonium chloride to the cooling vessel and maintain permanent stirring.

13. Charge 1.1% Methylchloroisothiazolinone. Cool the premix to 22° C. prior to proceeding charge to the vessel and maintain stirring.

14. Charge 5.5% Glutaric acid dialdehyde to the vessel. Maintain stirring until a uniform cream is achieved. Add any remaining material including pigments or fragrances to match individual requirements.

15. Intermediate Quality control check (a) Obtain a 1 liter sample.

(b) Quality control to ensure that a smooth slurry is obtained.

(b) Samples—Take 2 samples and issue them to the laboratory.

(c) Transfer—Ensure transfer IBC's are clean. Check the valve carefully.

Product Specification

Clarity=light index <600

Visual=slurry

Bubbles=various sized bubbles which reflect light and remain pH as LM 1620=6.0 to 6.3

Viscosity match to resin requirement @ 20° C.

Phase 2: Biocide Phase

Phase 2 of our process is the biocide phase. The uniform distribution is critical to the performance of the finished product. The addition of aqueous components to non-aqueous components is the process of creating an emulsion. In most cases emulsions are not stable and they require repeated mixing. During our research we have identified a method of reducing particle size at the ion level and by calculating the polarity of the existing components we have created a micro-emulsion that is both stable and functional.

The requirement of creating a stable structure is critical to the Alkyl Alcohols. The category C6 to C13 is a family of saturated alcohols that are produced from olefins by the hydroformylation or "oxo" process. The number of carbon atoms in the hydrotrope chain ranges from 6 to 13 and contain predominantly branched alkyl groups. Hydroformylation is the reaction of an olefin with carbon monoxide and hydrogen to produce an aldehyde, and its subsequent hydrogenation to the alcohol. Each substance consists of an isomeric mixture of saturated primary alcohols of high purity and the following basic structure: CH3-R—CH2-OH, where R is a branched isomeric structure. The ethoxylation rule is the higher the number the more hydrophilic the structure will become as this is an aqueous phase. Our development has been to maximise the solubility of an insoluble mixture. This is achieved by driving down the eo group to between 3 and 7 moles complimenting the phase 1 alcohol chain lengths of C8>C14 and 6 moles of ethoxylation but above 3 in order to balance out the chemical compatibility of phase 1 and 2.

Method of Manufacture: Micelle micro dispersion

This premix is added to the final batch: 1%

Batch Size: 20 Kg

1. Ensure all equipment is clean.

2. Lock the homogenization unit.

3. Set the stirring speed of the vessel to 200 r.p.m.

4. Charge warm alcohol ethoxylate to the primary high speed shearer mixing vessel at ~75° C.

5. Dispersion (a) Transfer product into the main mixing tank at a rate of 600 grams per second.

(b) Add the following raw materials in the order they are listed, which should be charged to the vessel:

42.0% Ethoxylate Alcohol, Laureth-7

6.0% *Pinus sylvestris*

48.0% Cetyl Alcohol wax 4.0% Propan-2-ol (c) Run until homogeneous (d) Start cooling at ~5° C. per minute until it is ~12° C., then transfer to a holding tank.

6. Run washout program on the mixing vessel

7. Intermediate Quality Control check (a) Obtain a 1 liter sample.

(b) Quality control to ensure that a smooth slurry is obtained.

(b) Samples—Take 2 samples and issue them to the laboratory.

(c) Transfer—Ensure transfer IBC's are clean. Check the valve carefully.

Product Specification

Clarity=light index<600

Visual=slurry

Bubbles=various sized bubbles which reflect light and remain pH as LM 1620=6.0 to 6.3

Viscosity match to resin requirement @ 20° C.

7. Intermediate Quality Control check

Obtain a 1 liter sample. QC to ensure smooth slurry is obtained.

Initialed by QC to complete a lab sample. Initialed by QC

8. Samples. Take 2 samples and issue to lab.

9. Transfer. Ensure transfer lines are clean. Check the VALVE carefully.

QC Testing
Product Specification
Clarity=clear
Visual=liquid dispersion
pH as LM 1620=6.3–7.0
Viscosity as LM 180=RVT 2/20 @ 20° C.=

The amphoterics provide the paring function, balancing out the base and acid characteristics of the other components, acting as a hydrotrope. The amphoteric components assist in the formation of the micro-dispersion by helping to regulate the particle size of the active ingredients.

Phase 3: Final Phase

Phase 3 is the final stage of the process, which is the bringing together of phase 1 and phase 2 of the process. The sealant manufacturing method requires optimum temperature and shear control to achieve uniform distribution. The optimum ratio of 4:1:95 of the dispersion phase one to phase two has shown the greater performance over a wide range of additions in to varnish, sealant or ink. Polyatomic cations are a product with antibacterial properties. They form a selective group of compounds that have been measured against specific organisms. The cationic substances are all water soluble and hydrophilic. They are insoluble in the hydrocarbon resin substrate. So a process of dispersion is required. Particle size is a key aspect to this process. Once a uniform dispersion is achieved, the key phase of micro-emulsion suspension can begin.

Method of Manufacture: Antimicrobial blending
Batch Size: 1000 Kg
Raw material: Resin base 950 Kg, Phase 1 addition 40 kg, Phase 2 addition 10 kg 1. Ensure all equipment is clean.
2. Lock the homogenization unit.
3. Set stirring speed of vessel to 80 r.p.m.
4. Charge the mixing tank with resin, sealant or coating. Warm to ~75° C.
5. Dispersion.
    (a) Transfer the Phase 1 product to the mixing tank at a rate of 60 grams per second. Do not exceed this amount.
    (b) Run until the homogeneous mix is achieved.
    (c) Transfer the Phase 2 product at a rate of 120 grams per second.
    (d) Run high shear at 600 r.p.m until homogeneous.
    (e) Stop the transfer pump once the required weight is achieved.
    (f) Close the valve network.
    (g) Start the heater and increase the heat to 60° C. Hold for 80 minutes whilst the solvent is flashed off.
    (h) Run high speed shearer up to 1200 r.p.m and run for 10 minutes.
    (i) As the product clears the 'micelle point' slow the mixer to 80 r.p.m.
    (j) Run for 40 minutes to allow air generated from mixing to rise to the surface.
    (k) Start the cooling process to fix micro emulsions. Cool to 15 to 20° C.
    (l) Place under a vacuum for 60 minutes to remove any excess air.
    (m) Quarantine the product prior to placing in to bulk storage, or placing on the production filling line.

The solvent addition is part of the manufacturing process but it is not an active addition. It is used to regulate the final viscosity and can only be used for Quality Control sign of to match the required end point. For the production of antimicrobial inks, coatings or varnishes, ink or the appropriate bases for coatings and varnishes are substituted for the resin used to produce sealants.

6. Intermediate Quality control check
    (a) Obtain a 1 liter sample.
    (b) Quality control to ensure that a smooth opaque slurry is obtained.
    (b) Samples—Take 2 samples and issue them to the laboratory.
    (c) Transfer—Ensure transfer IBC's are clean. Check the valve carefully.

Final quality control measures of print sealants
Quality test procedures for oil based varnishes
Testing procedures (viscosity)

The viscosity or body of an oil based sealer or overprint varnish is its resistance to flow. Printers describe the body of an ink or varnish as short, long, buttery or "like water". This is because inks and varnishes are non-Newtonian; therefore, it is not possible to define their viscosity with a single reading. Viscosity is one of the components that affects the tack of an oil based sealer or overprint varnish. Therefore, the two characteristics must be considered together. Any alteration made to adjust the viscosity will change the tack and vice versa.

The Bohlin Viscometer: To measure the viscosity of an oil based sealer or overprint varnish at varying rates of stress, which produces a graph, all of which are relevant to adequately define the rheology of the product.

Viscometer: The Bohlin CSR-10 Rheometer is linked to a computer. Thermo-circulator water bath @ 25° C. to control temperature The Bohlin rheometer is positioned in a temperature controlled room at 20° C.+/−2° C. and the base plate of the of the rheometer is connected to a thermo-circulator water bath @ 25° C. The Bohlin rheometer is checked on a monthly basis and serviced and calibrated yearly by the manufacturer in order to ensure that the correct settings are maintained.

Approximately 0.3 grams of a sample is placed in the centre of the plate of the rheometer. The exact volume is not critical provided that sufficient is present to fill the gap between the plate and the base. Any excess of the sample is squeezed out and should be scraped away. Under the instrument heading viscosity using the instrument settings described below:

Pre shear
Gap setting: 0.20 mm
Plate type: PP20
Shear stress: 2000 Pa
Apply time: 5 seconds
Equilibrium time: 60 seconds
Test parameters for the table of stress
Range: 24-4700 Pa
Number of readings: 15 seconds
Results: Logarithmic
Delay time: 5 seconds
Maximum time out: 5 seconds
Proportionality: Strain
Ramp: Up The test is carried out by clicking with the mouse on the start button on the screen. The parameters (pvw) and data (dvw) for each for each test are saved both on the hard drive and on a disk using the same batch number reference. The results are shown as a graph (viscosity in poises against sheer stress in Pa). Four points are taken from the table at 108, 489.5, 1517.1 and 4700 Pa. The viscosity of the sample is taken at these points and recorded on the batch card in QC. The figures/graph is compared to the standard/product specification for the formulation. If the figures/graph deviates from the required viscosity parameters, appropriate additions are made to the batch to bring it into specification.

Testing Procedures (Tack)

Tack or stickiness of an ink is defined as a measure of the cohesion of the wet film of an oil based sealer or overprint varnish (resistance to the film splitting). A varnish with a high degree of tack requires more force to split the film than a varnish which is less tacky. Tack is believed to be a function of plastic viscosity, elasticity and surface tension, all of which are dependent on the rate of shear.

The tack of a product is determined using a tack meter, which measures the tack or stickiness of a varnish by means of determining the torque produced by a series of rotating varnished rollers. The tack measurement recorded is in arbitrary units.

Viscosity is one of the components that affects the tack of an oil based sealer or overprint varnish, therefore, the two characteristics must be considered together. Any alteration made to adjust viscosity will change the tack and vice versa.

Tack-O-Scope tack meter: Thermo-circulator water bath @ 25° C. to control temperature. Digital scales accurate to two decimal places. The Tack-O-Scope is positioned in a temperature controlled room at 20° C.+/−2° C. and the centre roller is connected to a thermo-circulator water bath @ 25° C.

A weight 0.30 grams of the sample is accurately weighed and transferred on to the distribution roller and distributed across the distribution roller, centre roller and measuring roller at 50 rpm for 30 seconds. The speed of the Tack-O-Scope is raised to 200 rpm. The tack reading is recorded after a further 60 seconds.

Testing Procedures (Drying Time on Glass)

The drying time of an ink is defined as the point when a coherent skin is formed. This is taken as the point where the skin is sufficiently strong to be torn by the needle of the BK Drying Recorder. It is vital to measure or check the drying time of an oil based varnish to ensure that it dries consistently to give a rub resistant, protective film over printed matter. The drying time of a varnish will be dependent on the application with some products having very quick drying times and others, requiring "stay open" properties in the duct, having extended times.

Equipment: BK Drying time recorder in an incubator @ 32° C. BK wet film applicator cube—38 µm. 30 cm×2 cm glass slides. Using the wet film applicator cube, a film of 38 µm of the sample/batch is applied along the length of one of the glass slides. The same procedure is carried out using the standard product for comparative test results. The slides are placed on the BK Drying Recorder housed in the 32° C. incubator for the drying time to be recorded. The drying time is read off against the calibrated scale, being measured as the distance from the original point of contact of the stylus on the varnish to the point where the film is sufficiently coherent to be torn by the stylus rather than just parted.

Test results are recorded in hours and fractions of hours (¼, ½, and ¾). They are then checked against the specification and the reading obtained from the standard sample. A variance of +/−1 hour against the standard is considered an acceptable variance.

If the drying time of the batch deviates from the standard or specification, small additions of drier or anti-oxidant should be made and the batch retested in order to bring it within the required specification. These values are calculated on the basis of the active quotient used within our selected components. The values are expressed as a percentage of the final weight of the product.

Check the weights for Quality Control sign off:

| Components | Phase one additions | Phase two additions | Optimal addition of final batch |
|---|---|---|---|
| Ethylenediaminetetraacetic acid | 6.2 | 0.0 | 5.0 |
| 2-Hydroxypropanoic acid | 3.7 | 0.0 | 3.0 |
| Ethoxylate Alcohol, Laureth-7 | 14.2 | 42.0 | 19.7 |
| Cetyl alcohol wax | 14.2 | 48.0 | 20.9 |
| 12-hydroxy-9-cis-octadecenoic acid | 10.9 | 0.0 | 8.7 |
| Octadecenoic acid | 10.9 | 0.0 | 8.7 |
| Epoxy-cis-9-octadecenoic acid | 8.9 | 0.0 | 7.1 |
| Palmityl alcohol | 8.9 | 0.0 | 7.1 |
| Pinus sylvestris | 2.5 | 6.0 | 3.2 |
| Propan-2-ol | 0.0 | 4.0 | 0.8 |
| Methylchloroisothiazolinone | 1.1 | 0.0 | 0.9 |
| Didecyldimethylammonium chloride | 3.3 | 0.0 | 2.7 |
| Alkyldimethylbenzylammonium chloride | 5.4 | 0.0 | 4.4 |
| Glutaric acid dialdehyde | 5.5 | 0.0 | 4.4 |
| Parachlorometaxylenol | 4.4 | 0.0 | 3.6 |
| TOTALS | 100.0 | 100.0 | 100.0 |

| Components | Optimum value | Phase one as added to final batch | Phase two as added to final batch |
|---|---|---|---|
| Ethylenediaminetetraacetic acid | 0.25 | 5.0 | 0.0 |
| 2-Hydroxypropanoic acid | 0.15 | 3.0 | 0.0 |
| Ethoxylate Alcohol, Laureth-7 | 0.99 | 11.3 | 8.4 |
| Cetyl alcohol wax | 1.05 | 11.3 | 9.6 |
| 12-hydroxy-9-cis-octadecenoic acid | 0.43 | 8.7 | 0.0 |
| Octadecenoic acid | 0.43 | 8.7 | 0.0 |
| Epoxy-cis-9-octadecenoic acid | 0.35 | 7.1 | 0.0 |
| Palmityl alcohol | 0.35 | 7.1 | 0.0 |
| Pinus sylvestris | 0.16 | 2.0 | 1.2 |
| Propan-2-ol | 0.04 | 0.0 | 0.8 |
| Methylchloroisothiazolinone | 0.04 | 0.9 | 0.0 |
| Didecyldimethylammonium chloride | 0.13 | 2.7 | 0.0 |
| Alkyldimethylbenzylammonium chloride | 0.22 | 4.4 | 0.0 |
| Glutaric acid dialdehyde | 0.22 | 4.4 | 0.0 |
| Parachlorometaxylenol | 0.18 | 3.6 | 0.0 |
| TOTALS | 5.00 | 80.0 | 20.0 |

The manufacture of Phase one and two includes key elements of the design. The technology is unique in the print industry. The amalgamation of active substances combined with emulsified fatty alcohols create a primary solution that when mixed with an aqueous print sealant, an Ultra violet light activated varnish, a silicone suspension print finishing medium, print ink and an oil base print coating will provide antimicrobial properties. The supplemental independent testing carried out by an industry expert in antimicrobial products has conducted a study using the European Standard ratified by ISO test method to validate our claim. A European Standard (EN) is a standard that has been adopted by one of the three recognised European Standardisation Organisations (ESOs): CEN, CENELEC or ETSI. It is produced by all interested parties through a transparent, open and consensus based process. European Standards are a key component of the Single European Market. Although rather technical and often unknown to the public and media, they represent one of the most important issues for businesses. Often perceived as boring and not particularly relevant to some organisations, they are actually crucial in facilitating trade and hence have high visibility among manufacturers inside and outside Europe. A standard represents a model specification, a technical solution against which a market can trade. It codifies best practice and is usually state of the art. In essence, European Standards relate to products, services or systems. Today, however, standards are no longer created solely for technical reasons but have also become platforms to enable greater social inclusiveness and engagement with technology, as well as convergence and interoperability within growing markets across industries. The product can be adopted for use within the printing industry that provides a universal product for printing with Ink, Coatings, Sealants and print finishing to provide permanent antibacterial protection to greater than Log 3 (Log 3 is the test protocol minimum standard) although we have repeatedly achieved higher than log 4.

Compatibility Factors

Colour

The process will work with any colour or colourless coating used in the printing and print finishing industry.

Texture

The process can work with textured and non-textured printing and coating systems.

Surface Protection

The coating once sealed will form a water resistant permanent barrier providing additional protection against ingress of microbial organisms. The function by creating a physical barrier between the surface and contact with microorganisms the coating will prevent the transfer of infectious microorganisms between the two parties. We have developed a process by which the surfaces are rendered antimicrobial and will themselves kill infectious microorganisms on contact.

Variables

The optimal ratios in terms of volume between Phase 1, Phase 2 and the base in Phase 3 are 4:1:95. The preferred ratio in terms of the volumes of Phase 1 and Phase 2 is between 6:1 and 3:2. The preferred proportion in terms of volume of the base of Phase 3 is between 60% and 99%.

Lesser versions of the product could instead comprise in Phase 1: Glutaric acid dialdehyde, *Pinus sylvestris*, Ethoxylate Alcohol Laureth 7, Fatty alcohols, Didecyldimethylammonium chloride, Alkyldimethylbenzylammonium chloride, Parachlorometaxylenol, Non-ionic surfactants, Ethylenediaminetetraacetic acid, Methylchloroisothiazolinone; and in Phase 2 comprise Ethoxylate Alcohol Laureth-7, Cetyl alcohol wax, *Pinus sylvestris*, Propan-2-ol.

Uses

Some of the potential uses are Medical packaging (card medium, box packaging, packaging, paper products, stationery, note pads, medical equipment packaging, medical note paper, prescriptions, pulp screens, consumables, dry paper towels), and General pulp products (such as bank notes, brochures, catalogues, posters, point of sale, flyers, business cards, reports).

INDUSTRIAL APPLICABILITY

Antimicrobial inks, sealants, coatings or varnishes that are manufactured in three distinct phases: Phase 1, which is an oil phase comprising Ethoxylate Alcohol Laureth 7, Didecyldimethylammonium chloride, Glutaric acid dialdehyde, *Pinus sylvestris*, Alkyldimethylbenzylammonium chloride, Parachlorometaxylenol, Ethylene diaminetetraacetic acid, Cetyl alcohol wax, 2-Hydroxypropanoic acid, Hydroxy-9-cis-octadecenoic acid, Octadecenoic acid, Palmityl alcohol, and Epoxy-cis-9-octadecenoic acid; Phase 2, which is a micro-emulsion phase comprising Ethoxylate Alcohol Laureth-7, Cetyl alcohol wax, *Pinus sylvestris*, and Propan-2-ol and Phase 3, which combines the products of Phases 1 and 2 with a base to produce the ink, sealant, coating or varnish.

The invention claimed is:

1. An antimicrobial ink and sealant manufactured in three phases:
   phase 1, an oil phase, comprising (vol/vol %) 3% to 6% glutaric acid dialdehyde, 5% to 22% ethoxylate alcohol laureth 7, 2% to 5% didecyldimethylammonium chloride, 3% to 6% alkyldimethylbenzylammonium chloride, 1% to 5% *pinus sylvestris*, 6% to 12% octadecenoic acid, 4% to 11% epoxy-cis-9-octadecenoic, 6% to 22% cetyl alcohol wax, 4% to 12% hydroxy-9-cis-octadecenoic acid, 2% to 6% parachlorometaxylenol, 2% to 7% ethylenediaminetetraacetic acid, 1% to 4% 2-hydroxypropanoic acid, 0.25% to 2% methylchloroisothiazolinone, 3% to 10% palmityl alcohol;
   phase 2, a microemulsion phase, comprising (vol/vol %) 22% to 50% ethoxylate alcohol laureth-7, 22% to 50% cetyl alcohol wax, 2% to 6% propan-2-ol, 5% to 7% *pinus sylvestris*; and
   phase 3, comprising phase 1 and phase 2 with a resin base.

2. The antimicrobial ink and sealant according to claim 1, wherein the optimal amounts for phase 1 are (vol/vol %) 5.5% glutaric acid dialdehyde, 14.2% ethoxylate alcohol laureth 7, 3.3% didecyldimethylammonium chloride, 5.4% alkyldimethylbenzylammonium chloride, 2.5% *pinus sylvestris*, 10.9% octadecenoic acid, 14.2% cetyl alcohol wax, 4.4% parachlorometaxylenol, 8.9% epoxy-cis-9-octadecenoic, 10.9% hydroxy-9-cis-octadecenoic acid, 6.2% ethylenediaminetetraacetic acid, 3.7% 2-hydroxypropanoic acid, 1.1% methylchloroisothiazolinone, 8.9% palmityl alcohol; and
   wherein the optimal quantities in phase 2 are (vol/vol %) 42% ethoxylate alcohol laureth-7, 48% cetyl alcohol wax, 4% propan-2-ol, 6% *pinus sylvestris*.

3. The antimicrobial ink and sealant according to claim 1, wherein the optimal volumetric ratio of phase 1 to phase 2 to the base in phase 3 are 4:1:95.

4. The antimicrobial ink and sealant according to claim 1, wherein the optimal volumetric ratio of phase 1 to phase 2 ranges between 6:1 and 3:2.

5. The antimicrobial ink and sealant according to claim 1, wherein the base in phase 3 is present in an amount ranging between 60% and 99% in volume.

6. An antimicrobial ink, sealant, coating or varnish comprising an additive manufactured in two phases:
   phase 1, an oil phase, comprising (vol/vol %) 3% to 6% glutaric acid dialdehyde, 5% to 22% ethoxylate alcohol laureth 7, 2% to 5% didecyldimethylammonium chloride, 3% to 6% alkyldimethylbenzylammonium chloride, 1% to 5% *pinus sylvestris*, 6% to 12% octadecenoic acid, 4% to 11% epoxy-cis-9-octadecenoic, 6% to 22% cetyl alcohol wax, 4% to 12% hydroxy-9-cis-octadecenoic acid, 2% to 6% parachlorometaxylenol, 2% to 7% ethylenediaminetetraacetic acid, 1% to 4% 2-hydroxypropanoic acid, 0.25% to 2% methylchloroisothiazolinone, 3% to 10% palmityl alcohol; and
   phase 2, a microemulsion phase, comprising (vol/vol %) 22% to 50% ethoxylate alcohol laureth-7, 22% to 50% cetyl alcohol wax, 2% to 6% propan-2-ol, 5% to 7% *pinus sylvestris*.

\* \* \* \* \*